US008298759B2

(12) United States Patent
Voloshin et al.

(10) Patent No.: US 8,298,759 B2
(45) Date of Patent: Oct. 30, 2012

(54) PROTEIN EXPRESSION YIELD ENHANCEMENT IN CELL-FREE PROTEIN SYNTHESIS SYSTEMS BY ADDITION OF ANTIFOAM AGENTS

(75) Inventors: Alexei M. Voloshin, Newark, CA (US); James Robert Swartz, Menlo Park, CA (US)

(73) Assignee: The Board of Trustee of the Leland Stanford Junior University, Palo Alto, CA (US)

( * ) Notice: Subject to any disclaimer, the term of this patent is extended or adjusted under 35 U.S.C. 154(b) by 980 days.

(21) Appl. No.: 10/599,310

(22) PCT Filed: Mar. 21, 2005

(86) PCT No.: PCT/US2005/009342
§ 371 (c)(1),
(2), (4) Date: Oct. 20, 2008

(87) PCT Pub. No.: WO2005/098048
PCT Pub. Date: Oct. 20, 2005

(65) Prior Publication Data
US 2009/0042244 A1 Feb. 12, 2009

(51) Int. Cl.
*C12Q 1/68* (2006.01)
*C07K 1/00* (2006.01)
(52) U.S. Cl. ......................................... 435/6.1; 530/350
(58) Field of Classification Search ........................ None
See application file for complete search history.

(56) References Cited

U.S. PATENT DOCUMENTS

| | | | |
|---|---|---|---|
| 3,990,905 A * | 11/1976 | Wachala et al. | 127/44 |
| 5,223,412 A | 6/1993 | Wight et al. | |
| 5,547,841 A | 8/1996 | Marotta et al. | |
| 5,856,174 A * | 1/1999 | Lipshutz et al. | 435/286.5 |
| 6,337,191 B1 | 1/2002 | Swartz et al. | |
| 6,518,058 B1 | 2/2003 | Biryukov et al. | |
| 6,664,078 B1 | 12/2003 | Schmidt et al. | |
| 2005/0123924 A1* | 6/2005 | Rashtchian et al. | 435/6 |
| 2007/0154983 A1* | 7/2007 | Calhoun et al. | 435/69.1 |

FOREIGN PATENT DOCUMENTS

| | | |
|---|---|---|
| CA | 2 486 913 | 11/2003 |
| CA | 2486913 A1 | 11/2003 |
| JP | 04-200390 | 7/1992 |

OTHER PUBLICATIONS

Nemeth; et al., "Foam Control by Silicone Polyethers-Mechanisms of "Cloud Point Antifoaming"", J. Colloid. Interface Sci. (1998), 207(2):386-394.
Zhang; et al., "Foaming and media surfactant effects on the cultivation of animal cells in stirred and sparged bioreactors", J. Biotechnol. (1992), 25(3):289-306.
Adachi; et al., "Effects of heme addition on formation of stable human globin chains and hemoglobin subunit assembly in a cell-free system", Archives of Biochemistry and Biophysics (2003), 413: 99-106.
Mostafa; et al., "Strategies of Improved $dCO_2$ Removal in Large-Scale Fed-Batch Cultures", Biotechnol. Prog. (2003), 19:45-51.
Wongsamuth; et al., "Foaming and Cell Flotation in Suspended Plant Cell Cultures and the Effects of Chemical Antifoams", Biotechnology and Bioengineering (1994), 44:481-488.
Kim, Dong-Myung; et al., "Regeneration of Adenosine Triphosphate from Glycolytic Intermediates for Cell-Free Protein Synthesis", Biotechnology and Bioengineering, Aug. 20, 2001, 74(4):309-16.
Cha et al. "Green Fluorescent Protein as a Noninvasive Stress Probe in Resting *Escherichia coli* Cells" Applied & Environmental Microbiology, Feb. 1999, vol. 65, No. 2, pp. 1999-2002.
Cock et al. "Affinity of the periplasmic chaperone Skp of *Escherichia coli* for phospholipids, lipopolysaccharides and non-native outer membrane proteins" European Journal of Biochemistry, Jan. 1999, vol. 259(1-2):96-103.
Davanloo et al. "Cloning and Expression of the Gene for Bacteriophage T7 RNA Polymerase" PNAS, Apr. 1984, vol. 81(7):2035-2039.
Gill et al. "Calculation of protein extinction coefficients from amino acid sequence data" Analytical Biochemistry, Nov. 1, 1989, vol. 182(2):319-326.
Hakim et al. "A nine-amino acid peptide from IL-1beta augments antitumor immune responses induced by protein and DNA vaccines" Journal of Immunology, 1996, vol. 157:5503-5511.
Hellwig et al. "Plant Cell Cultures for the Production of Recombinant Proteins" Nature Biotechnology, Nov. 2004, vol. 22, No. 11, pp. 1415-1422.
Kim et al. "A Highly Efficient Cell-Free Protein Synthesis System from *Escherichia coli*" European Journal Biochemistry, Aug. 1996, vol. 239(3): 881-886.
Kim et al. "Expression-independent consumption of substrates in cell-free expression system from *Escherichia coli*" Journal of Biotechnology, 2000, vol. 84:27-32.
Kim et al. "Oxalate Improves Protein Synthesis by Enhancing ATP Supply in a Cell-Free System Derived from *Escherichia coli*" Biotechnology Letters, 2000, vol. 22, pp. 1537-1542.
Kim et al. "Prolonging Cell-Free Protein Synthesis by Selective Reagent Additions" Biotechnology Progress, 2000, vol. 16(3):385-390.
Pratt "Coupled Transcription—Translation in Prokaryotic Cell-Free Systems" 1984, Hames BD, Higgins SJ. Ed. in Transcription and Translation: A Practical Approach. New York IRL Press:179-209.
Tao et al "Idiotype/granulocyte-macrophage colony-stimulating factor fusion protein as a vaccine for B-cell lymphoma" Nature, Apr. 22, 1993, vol. 362:755-758.

* cited by examiner

*Primary Examiner* — Young J Kim
(74) *Attorney, Agent, or Firm* — Bozicevic, Field & Francis LLP; Pamela J. Sherwood

(57) ABSTRACT

Compositions and methods are provided for the in vitro synthesis of biological molecules in reaction mixtures comprising anti-foam agents. The reaction mix comprising antifoam agent may be a scaled up reaction, e.g. in reaction volume greater than at least about 15 μl. Reactions may be performed in various reactors, as known in the art, which include stirred reactors, bubble-column reactors; and the like.

13 Claims, 4 Drawing Sheets

PROTEIN EXPRESSION YIELD ENHANCEMENT IN CELL-FREE PROTEIN SYNTHESIS SYSTEMS BY ADDITION OF ANTIFOAM AGENTS

FEDERALLY-SPONSORED RESEARCH OR DEVELOPMENT

This invention was made with Government support under contract CA034233 awarded by the National Institutes of Health. The Government has certain rights in this invention.

BACKGROUND OF THE INVENTION

Protein synthesis is a fundamental biological process, which underlies the development of polypeptide therapeutics, diagnostics, and catalysts. With the advent of recombinant DNA (rDNA) technology, it has become possible to harness the catalytic machinery of the cell to produce a desired protein. This can be achieved within the cellular environment or in vitro using extracts derived from cells.

Over the past decade, the productivity of cell-free systems has improved two orders of magnitude, from about 5 µg/ml-hr to about 500 µg/ml-hr. This accomplishment has made in vitro protein synthesis a practical technique for laboratory-scale research and provides a platform technology for high-throughput protein expression. It also begins to suggest the feasibility of using cell-free technologies as an alternative means to the in vivo large-scale production of protein pharmaceuticals.

Cell-free protein synthesis offers several advantages over conventional, in vivo, protein expression methods. Cell-free systems can direct most, if not all, of the metabolic resources of the cell towards the exclusive production of one protein. Moreover, the lack of a cell wall in vitro is advantageous since it allows for better control of the synthesis environment. For example, tRNA levels can be changed to reflect the codon usage of genes being expressed. Also, the redox potential, pH, or ionic strength can be altered with greater flexibility than in vivo since cell growth or viability is not a concern. Furthermore, direct recovery of purified, properly folded protein products can be easily achieved.

In vitro translation is also recognized for its ability to incorporate unnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo, and is becoming a platform technology for this field.

Despite all of the promising features of cell-free protein synthesis, its practical use and large-scale implementation has been limited by several obstacles. Paramount among these are short reaction times and low protein production rates, which lead to poor yields of protein synthesis and excessive reagent cost. The pioneering work of Spirin et al. (1988) *Science* 242:1162-1164 initially circumvented the short reaction times problem with the development of a continuous flow system. Many laboratories have duplicated and improved upon this work, but they have all primarily used methods that constantly supply substrates to the reaction chamber. This approach increases the duration of the translation reaction and protein yield as compared to the batch system. However, it is inefficient in its use of expensive reagents, generally produces a dilute product, and has not provided significant improvements in production rates.

The conventional batch system offers several advantages over these continuous and semi-continuous schemes, which include ease of scale-up, reproducibility, increased protein production rates, convenience, applicability for multi-plexed formats for high throughput expression, and more efficient substrate use. These advantages make improving the batch system productivity crucial for the industrial utilization of cell-free protein synthesis. However, using current methodology, when reactions are scaled up there is a loss of efficiency. The decrease in specific protein product yield is especially severe in the systems that require oxygen for oxidative phosphorylation. Increasing the product yield in larger reactions is an essential component of filling this need.

Relevant Literature

U.S. Pat. No. 6,337,191 B1, Swartz et al. Kim and Swartz (2000) *Biotechnol Prog.* 16:385-390; Kim and Swartz (2000) *Biotechnol Lett.* 22:1537-1542; Kim and Choi (2000) *J Biotechnol.* 84:27-32; Kim et al. (1996) *Eur J Biochem.* 239: 881-886; Tao and Levy (1993) *Nature* 362:755-758; Hakim et al. (1996) *J Immun.* 157:5503-5511; Pratt (1984) Coupled transcription-translation in prokaryotic cell-free systems. In: Hames B D, Higgins S J. Ed. In transcription and translation: a practical approach. New York: IRL press: 179-209.; Davanloo et al. (1984) *PNAS* 81:2035-2039; Cock et al. (1999) *Biochemistry* 259: 96-103; Gill and Hippel (1989) *Anal. Biochem.* 182:319-326; Kim et al. (1999) *Europ. J. Biochem.* 239: 881-886; Davanloo et al. (1984) *PNAS* 81:2035-2039

SUMMARY OF THE INVENTION

Compositions and methods are provided for the in vitro synthesis of biological molecules in reaction mixtures comprising anti-foam agents. Addition of antifoam agents to cell-free synthesis reactions enhances specific yield of protein in cell-free systems. In one embodiment of the invention, the reaction mix comprising antifoam agent is a scaled up reaction, e.g. in reaction volumes greater than at least about 15 µl. Reactions may be performed in various reactors, as known in the art, which include bubble-column reactors.

DETAILED DESCRIPTION OF THE EMBODIMENTS

Figure 1:
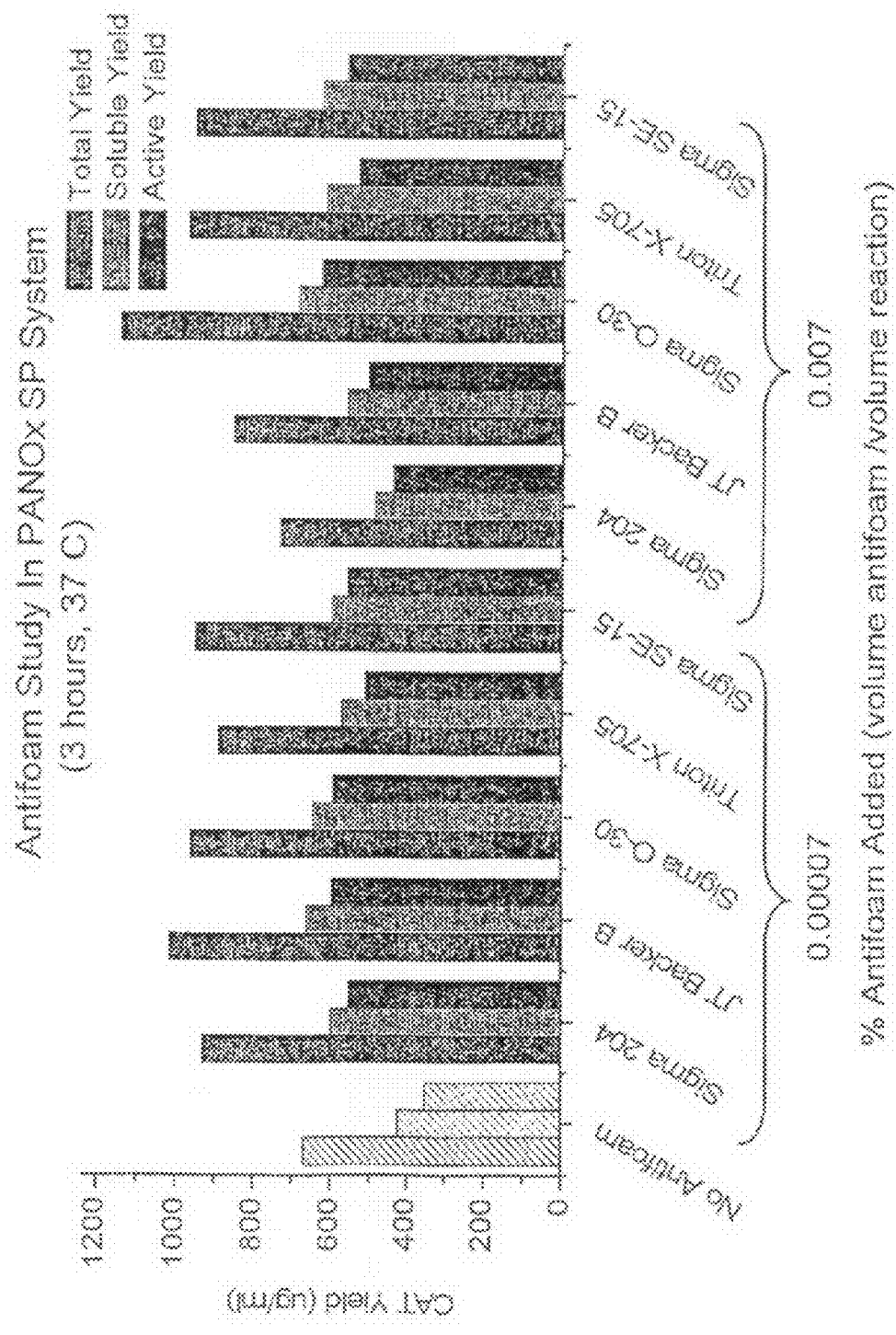
FIG. 1 is a graph depicting the protein yield in reactions comprising different antifoam agents.

Compositions and methods are provided for the in vitro synthesis of biological molecules in reaction mixtures comprising antifoam agents to enhance the total, soluble, and active yield of proteins synthesized in cell-free systems. The addition of antifoam can increase yield in small scale reactions, but finds particular benefit in larger scale reactions, particularly reactors providing for aerobic conditions.

In vitro synthesis, as used herein, refers to the cell-free synthesis of biological macromolecules in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001, herein incorporated by reference.

In one embodiment of the invention, the reaction chemistry is as described in co-pending patent application U.S. Ser. No. 10/643,683, herein incorporated by reference. Oxidative phosphorylation is activated, providing for increased yields and enhanced utilization of energy sources. Improved yield is obtained by a combination of factors, including the use of biological extracts derived from bacteria grown on a glucose containing medium; an absence of polyethylene glycol; and optimized magnesium concentration. This provides for a homeostatic system, in which synthesis can occur even in the absence of secondary energy sources.

It is well-known in the art that performance of bioreactors can change dramatically with scale. There are difficulties in maintaining homogeneity in large systems, changes in surface to volume ratios, and changes in the reactions themselves due to increased time frames. In addition to these problems, in vitro protein synthesis reactions that activate oxidative phosphorylation may require increased oxygen for optimal performance, the delivery of which becomes more difficult as reaction volume increases.

Among the more common types of reactors are included, without limitation, stirred tank reactors; bubble column reactors and air-lift reactors, which rely on gas sparging for agitation; etc. The bubble column reactor may be preferred for Cytomim reaction conditions.

A problem often encountered in commercial fermentation is foaming, which is undesirable, for various reasons, including providing a pathway for contaminating cells to enter the fermentor. Foam in cell cultures has been controlled with the addition of surface-acting chemical agents, although such anti-foam agents usually lower $K_L a$ values, reducing the reactor's capacity to supply oxygen and other gases, and may also inhibit cell growth. For in vitro synthesis, the hydrophobic components of antifoam would be expected to interfere with protein synthesis and folding, since the catalysts and nascent products are not protected within a cell as they are when proteins are expressed in vivo, e.g. by conventional recombinant expression methods. The results provided herein are therefore unexpected.

Antifoam Agents

The in vitro protein synthesis reactions of the present invention comprise an antifoam agent. The agent is usually present at a concentration of at least about 0.00007%, and may be at least about 0.0001%, and not more than about 0.001%, usually not more than about 0.007% by weight. Different control strategies, including fixed aliquot, on-demand control, and proportional, integral, and/or derivative control or a combination of them, can be employed to adjust the antifoam agent flow rate in continuous feed reactions. Optimum amounts of antifoam agent additions depend upon variables such as reaction conditions, antifoam agent type, and the like. Optimum amounts of antifoam agent addition; and where applicable the time span between additions, may be determined empirically during trial runs.

Antifoam agent, as used herein, is a surface acting chemical added to the reaction mixture to facilitate bubble breakage and gas release and to counteract the foaming that can be caused by mixing, sparging, or stirring. Antifoam agents may prevent; eliminate; and/or reduce foam. Antifoam agents may additionally impart positive ancillary surface properties, such as wetting, dispersion, emulsification, solubilization, flow and leveling, adhesion, and gloss.

Many chemical compounds can be used as antifoam agents, these include but are not limited to alkyl polyoxyalkylene glycol ethers; esters; alcohols; siloxanes; silicones; sulfites; sulfonates; fatty acids and their derivatives; etc. A variety of such agents are known and commercially available, e.g. through Sigma Chemicals; J. T. Baker; etc. In some embodiments of the invention, the antifoam agent is other than a detergent.

Among antifoam agents of interest are block copolymers, which provide defoaming/antifoaming action by forming an insoluble monolayer at the air/water interface of the foam. The defoaming activity of a block copolymer is a function of both the cloud point of the copolymer and the use temperature. To select an effective defoamer, a block copolymer is selected whose cloud point is lower than the intended use temperature. Block copolymers with low ethylene oxide content are the most effective defoamers. The PLURONIC® surfactants are widely used as defoamers. The reverse-structure PLURONIC® R surfactants are also effective in defoaming applications. Other antifoam agents of interest include siloxane polymers; mixtures of organic non-silicone polypropylene based polyether dispersions; organic, fatty acid ester-type antifoams; and the like.

Reaction Chemistry

The template for cell-free protein synthesis can be either mRNA or DNA. Translation of stabilized mRNA or combined transcription and translation converts stored information into protein. The combined system, generally utilized in *E. coli* systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally run between pH 6-9. The temperature of the reaction is generally between 20° C. and 40° C. These ranges may be extended.

Metabolic inhibitors to undesirable enzymatic activity may be added to the reaction mixture. Alternatively, enzymes or factors that are responsible for undesirable activity may be removed directly from the extract. Thirdly, the gene encoding the undesirable enzyme may be inactivated or deleted from the chromosome.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

Synthetic systems of interest include the replication of DNA, which may include amplification of the DNA, the transcription of RNA from DNA or RNA templates, the translation of RNA into polypeptides, and the synthesis of complex carbohydrates from simple sugars.

The reactions may be large scale, small scale, or may be multiplexed to perform a plurality of simultaneous syntheses. Additional reagents may be introduced to prolong the period of time for active synthesis. Synthesized product is usually accumulated in the reactor, and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include *E. coli* extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, spermine, spermidine, etc.

The salts preferably include potassium, magnesium, ammonium and manganese salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine and spermidine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 25°-40° C.

The amount of protein produced in a translation reaction can be measured in various fashions. One method relies on the availability of an assay that measures the activity of the particular protein being translated. Examples of assays for measuring protein activity are a luciferase assay system, and a chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in a combined in vitro transcription and translation reactions is to perform the reactions using a known quantity of radiolabeled amino acid such as $^{35}$S-methionine or $^{14}$C-leucine and subsequently measuring the amount of, radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Reaction Volumes and Geometries

While the reactions may be of any volume, the methods are particularly advantageous in a scaled up reaction, where the reaction volume is at least about 15 μl, usually at least about 50 μl, more usually at least about 100 μl, and may be 500 μl, 1000 μl, 5000 μl or greater. In many cases, individual reactions will not be more than about 10 ml, although multiple reactions can be run in parallel. However, it is also anticipated that the present invention will enable scale-up to much larger volumes, as used in commercial bioreactors, which may be configured for volumes of 1 liter, 10 liters, 100 liters, 1000 liters, or more. While the reaction mixture may comprise lipids, e.g. inverted vesicles, it is usually not bounded at the surface by lipid bilayers.

As used herein, the term "small scale" refers to reactions having a volume of about, or less than about, 15 μl. The methods of the present invention allow "scaled up" reactions, as described above, to maintain substantially consistent yields as compared to a small scale reaction. Yield may be calculated by any convenient method, as long as it is consistently applied between the reactions, e.g. total protein synthesis/ml reaction mixture; soluble protein synthesis/ml. reaction mixture; biologically active protein synthesis/ml. reaction mixture; and the like. The yield in a scaled up reaction, as compared to a comparable small scale reaction (i.e. a reaction comprises the same reactants, differing only in volume), is usually at least about 90%, more usually at least about 95%; and may be at least about 99%. In some cases it has been observed that the yield is actually increased in a scaled up reaction mixture of the present invention.

The system can be run under aerobic and anaerobic conditions, preferably aerobic. To prevent desiccation of the reaction, the headspace may be humidified, usually at least about 80% saturated at the working temperature, more usually at least about 90% saturated at the working temperature. Under laboratory conditions it is usually sufficient to seal the chamber enclosing the headspace. The headspace of the reaction chamber may be filled with oxygen or oxygen may be infused into the reaction mixture. Oxygen can be supplied continuously or the headspace of the reaction chamber can be refilled during the course of protein expression for longer reaction times. Besides oxygen, other electron acceptors, such as nitrate may also be supplied for cell extract previously induced for the appropriate respiration pathway.

Aerated reaction conditions may be provided in a bubble column design. In a bubble column, air is bubbled or sparged into the liquid filled container. The gas can be dispersed into bubbles by sparging the gas into the liquid phase, as in a column. The gas, e.g. oxygen or a mixture comprising oxygen, can be dispersed into bubbles through distribution plates covering the full area of the column, and also airlift reactors, in which the air is confined in a channel by means of a loop or draft tube designed to impart a certain type of overall circulatory pattern to the entire tank. A variety of column configurations are known in the art, and may include variations in size, baffles, head-space, etc. For example, see Bubble Column Reactions, 1$^{st}$ ed.; Wolf-Dieter Deckwer (Gesellschaft für Biotechnologische Forschung mbH, Braunschweig, Germany) ISBN: 0471918113; Oldshue (1983) Biotechnol Adv. 1(1):17-30; Poulsen & Iversen (1999) Biotechnol Bioeng. 64(4):452-8; Poulsen & Iversen (1998) Biotechnol Bioeng. 58(6):633-41; inter alia; herein incorporated by reference.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Figure 2:
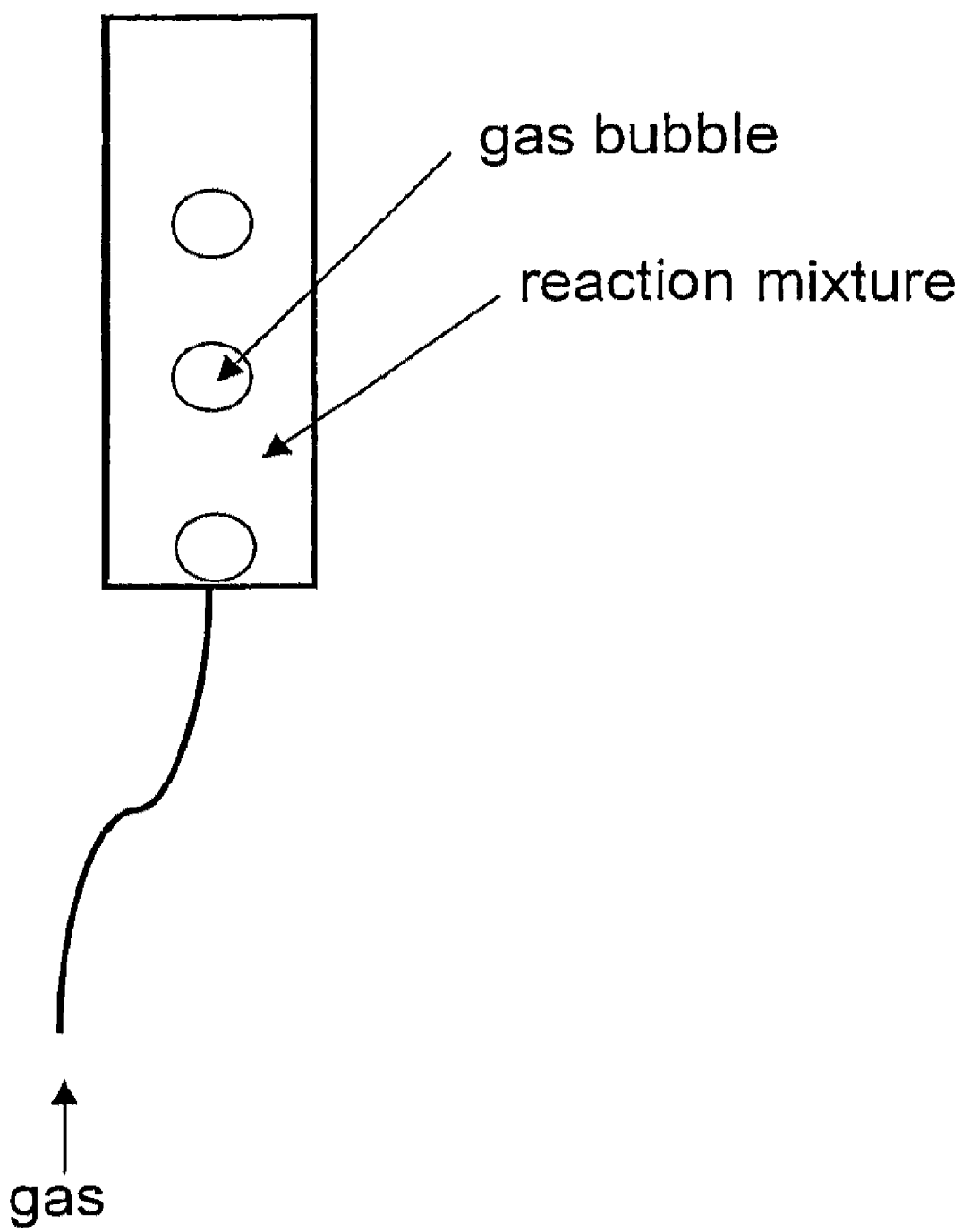
FIG. 2 is a schematic of a bubble reactor.
Figure 3:
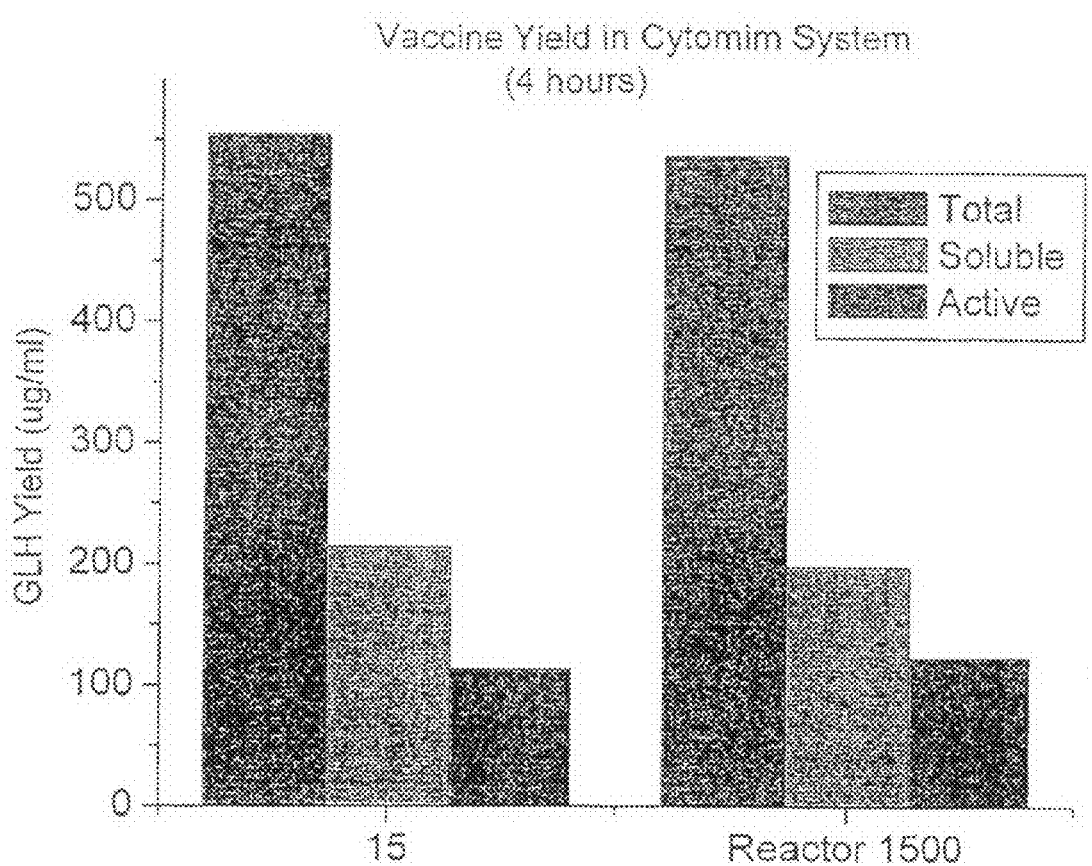
FIG. 3 is a graph depicting yields of the protein GMCSF-scFv in a bubble column with total reaction volumes of 1500 µl, compared to a 15 µl reaction.
Figure 4:
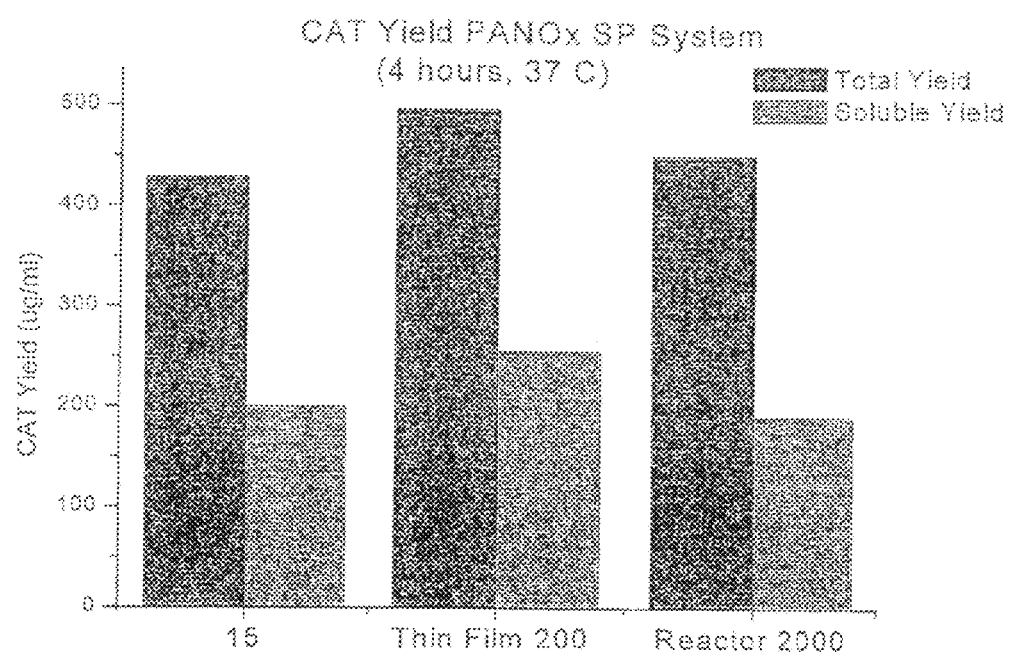
FIG. 4 is graph depicting yields in a bubble column with a reaction volume of 2000 µl, compared to the 200 µl thin film reaction, and a 15 µl Eppendorf tube reaction. With addition of antifoam, the specific yield in each system is comparable.

The addition of antifoaming agents to cell-free protein synthesis system was tested. Five different antifoams agents were added to the PANOx (Kim and Swartz 2001 Biotechnol. Bioengineer. 74:309-316) cell-free system and were found to enhance the total, soluble, and active yield of *E. coli* chloramphenicol acetyl transferase (CAT) (FIG. 1). FIG. 2 shows the basic outline of the bubble reactor. FIGS. 3 and 4 compare the yield of GMCSF-VL-VH mammalian protein construct and CAT in the bubble reactor at large scale vs. small scale in Eppendorf tubes. The agents are listed in Table 1, and reaction components in Tables 2 and 3.

For the cytomim system, the components listed in Table 2 are mixed in the indicated concentrations (Jewett and Swartz, co-pending application Ser. No. 10/643,683). For the PANOx system, the components listed in Table 3 are mixed in the indicated concentrations as described by Swartz and Kim, "Regeneration of Adenosine Triphosphate from Glycolytic Intermediates for Cell-Free Protein Synthesis", Biotechnology and Bioengineering, Vol. 74, 4, Aug. 20, 2001.

For the CAT protein expression, the DNA used as the template in the system is pK7-CAT circular plasmid that includes the T7 promoter followed by the gene encoding the *E. coli* protein Chloramphenicol Acetyl Transferase. The structural gene is followed by a T7 terminator.

For GMCSF-scFv protein expression, the DNA used as the template in the system is the pK7-GMCSF-VL-VH circular plasmid that includes the T7 promoter followed by the gene encoding the GMCSF protein (Mi-Hua Tao, 1993) and fused to the gene encoding the scFv fragment of the murine lymphoma antibody, 38C13 (Hakim, 1996) through a 5-amino acid linker (glycine$_4$-serine). The structural gene is followed by a T7 terminator.

S30 cell extract was prepared from *E. coli* K12 (strain A19) according to the procedures of Pratt (1984). No DL-dithiothreitol was added to the cell lysate after homogenization. T7 RNA polymerase was prepared from the culture of *E. coli* strain BL21 (pAR1219) according to the procedures of Davanloo et al (1984).

For GMCSF-VL-VH expression, the expression system was modified to enhance protein folding and disulfide bond formation using the following additions. Cell free extract is pretreated with 0.85 mM iodoacetamide (IAM) for 30 minutes at room temperature prior to addition to the reaction mixture. *E. coli* DsbC was added at 50 ug/ml concentration. Oxidized and reduced glutathione are added to the reaction mixture at concentrations of 4 mm and 1 mm, respectively.

*E. coli* DsbC was prepared by overexpressing strain BL21 (DE3) (pETDsbC) and was purified with a cobalt IMAC column. The selected fractions were dialyzed against S30 buffer (Pratt, 1984) containing 5 mM DTT to reduce the active site of DsbC.

The antifoam agents were purchased from the listed vendors, and added in the indicated amounts. In some cases the antifoam was diluted in water such as to add 1 μl of antifoam/water mixture to every 15 ul of cell-free reaction.

For the Eppendorf test tube method, the mixture of appropriate volume is pipetted on the bottom of an Eppendorf test tube. The tube is incubated at 37° C. for the appropriate period of time (3 hours for the PANOx, 6 hours for the Cytomim system).

TABLE 1

| Antifoam Name | Manufacturer |
|---|---|
| Antifoam 204 | Sigma |
| Antifoam B | J. T. Baker |
| Antifoam O-30 | Sigma |
| Triton X-705 | Sigma |
| Antifoam SE-15 | Sigma |

TABLE 2

Reagent make-up and concentrations for the Cytomim cell-free protein synthesis system.

| Reagent | Concentration |
|---|---|
| Magnesium Glutamate | 8 mM |
| Ammonium Glutamate | 10 mM |
| Potassium Glutamate | 130 mM |
| ATP | 1.20 mM |

TABLE 2-continued

Reagent make-up and concentrations for the
Cytomim cell-free protein synthesis system.

| Reagent | Concentration |
| --- | --- |
| GTP | 0.86 mM |
| UTP | 0.86 mM |
| CTP | 0.86 mM |
| Folinic acid | 34 ug/ml |
| tRNA | 170.6 ug/ml |
| 20 amino acids | 2 mM |
| Cysteine | 9 mM |
| Pyruvate | 30 mM |
| NAD | 3.3 mM |
| CoA | 2.7 mM |
| Oxalic Acid | 4 mM |
| Spermidine | 1.5 mM |
| Putrescine | 1 mM |
| T7 RNA polymerase | 0.10 mg/ml |
| Plasmid | 0.0133 mg/ml |
| S30 extract * | 6/25 total reaction volume |

TABLE 3

Reagent make-up and concentrations for the
PANOx cell-free protein synthesis system.

| Reagent | Concentration |
| --- | --- |
| Magnesium Glutamate | 20 mM |
| Ammonium Glutamate | 10 mM |
| Potassium Glutamate | 170 mM |
| ATP | 1.2 mM |
| GTP | 0.86 mM |
| UTP | 0.86 mM |
| CTP | 0.86 mM |
| Folinic Acid | 34 ug/ml |
| tRNA | 170.6 ug/ml |
| 20 Amino Acids | 2.0 mM |
| Phosphoenolpyruvate | 30 mM |
| NAD | 0.33 mM |
| CoA | 0.27 mM |
| Oxalic Acid | 2.70 mM |
| Putrescine | 1.00 mM |
| Spermidine | 1.50 mM |
| T7 RNA Polymerase | 0.1 mg/ml |
| Plasmid Template | 0.0133 mg/ml |
| S30 Extract * | 3.6 ul/15 ul RXN |

The bubble column reactor consists of a column with a diameter of 1 cm ID and 5 cm height. Cell-free reaction mixture (Tables 1 and 2) was pipetted inside the column (FIG. 2). Gas is bubbled through a small jet (less that 1 mm diameter) at the bottom of column from a compressed gas tank.

For the Cytomim system (as described by Jewett and Swartz, co-pending application Ser. No. 10/643,683), pure oxygen gas was used and the reaction lasted for a maximum of 4 hours at 37° C. For the PANOx reactions, argon gas was used and the reaction time was 3 hours at 37° C. The bubble size was approximately 0.5 cm in diameter and bubbling rate was approximately 1 bubble/second. Without addition of antifoam, the cell-free protein synthesis reaction immediately foams out of the top of the column reactor. No protein is produced. Upon addition of antifoam (Sigma 204, 1/1000-1/10000 volume antifoam/volume reaction), the protein synthesis reaction proceeds with minimal foaming for up to 3.5 to 4 hours producing protein yields comparable to those from 15 μl Eppendorf tube reactions (see FIGS. 3 and 4).

The amount of synthesized protein was estimated from the measured TCA-precipitated radioactivities in a liquid scintillation counter (LS3801, Beckman Coulter, Inc.). After centrifuging samples at 4° C. and 15,000 RCF for 15 minutes, supernatants were taken and used to determine soluble yield by TCA precipitation and scintillation counting. The procedures in detail were described previously (Kim et al, 1996 b).

Results are shown for CAT as well as for a GM-CSF-scFv fusion protein. The entire reaction is run in batch mode with no post-start additions.

These data demonstrate that, in different scales and with different reaction geometries and proteins, the addition of an antifoam agent provides for improved in vitro protein synthesis. In particular, the antifoam agents provide enhanced yield in a scale up reaction using a bubble-column.

What is claimed is:

1. A method for translation of mRNA to produce polypeptides, the method comprising:
synthesizing said polypeptides in a cell-free reaction mixture of greater than about 15 μl volume, comprising an antifoam agent at a concentration of at least 0.00007%, and not more than 0.007% by weight, wherein the antifoam agent is other than a detergent.

2. The method of claim 1 wherein said synthesizing also comprises transcription of mRNA from a DNA template.

3. The method of claim 1, wherein said reaction mix comprises a volume of greater than 100 μl.

4. The method of claim 3, wherein said reaction has a yield that is at least about 90% of the yield in a comparable reaction of less than 15 μl volume.

5. The method of claim 1 wherein oxidative phosphorylation is activated in the cell-free reaction mixture.

6. The method of claim 1 wherein said reaction mixture comprises a volume of greater than 1000 μl.

7. The method of claim 1, wherein said synthesizing is performed in a reactor.

8. The method of claim 7, wherein the reactor is a bubble reactor.

9. The method of claim 1, wherein the antifoam agent is selected from alkyl polyoxyalkylene glycol ethers; siloxane polymers; and mixtures of organic non-silicone polypropylene based polyether dispersions.

10. A method for translation of mRNA to produce polypeptides, the method comprising:
synthesizing said polypeptides in a cell free reaction mixture of greater than about 15 μl volume, comprising:
a cell extract; a template for production of the mRNA and/or polypeptides; monomers for the mRNA and/or polypeptides to be synthesized; and co-factors, enzymes and reagents that are necessary for the synthesis; and an anti-foam agent at a concentration of at least 0.00007%, and not more than 0.007% by weight, wherein the antifoam agent is other than a detergent.

11. The method of claim 10, wherein the antifoam agent is selected from alkyl polyoxyalkylene glycol ethers; siloxane polymers; and mixtures of organic non-silicone polypropylene based polyether dispersions.

12. A reaction mixture for cell-free translation of mRNA to produce polypeptides, comprising:
a cell extract; mRNA; monomers for the polypeptide to be synthesized; and co-factors, enzymes and reagents that are necessary for the synthesis; and an anti-foam agent other than a detergent at a concentration of at least 0.00007%, and not more than 0.007% by weight.

13. The reaction mixture of claim 12, wherein the antifoam agent is selected from alkyl polyoxyalkylene glycol ethers; siloxane polymers; and mixtures of organic non-silicone polypropylene based polyether dispersions.

* * * * *

UNITED STATES PATENT AND TRADEMARK OFFICE
CERTIFICATE OF CORRECTION

PATENT NO. : 8,298,759 B2
APPLICATION NO. : 10/599310
DATED : October 30, 2012
INVENTOR(S) : Voloshin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1067 days.

Signed and Sealed this
Twenty-sixth Day of February, 2013

Teresa Stanek Rea
*Acting Director of the United States Patent and Trademark Office*